United States Patent
Shinohaea et al.

(10) Patent No.: US 7,129,256 B2
(45) Date of Patent: Oct. 31, 2006

(54) ANTIPARKINSONISM DRUGS

(75) Inventors: Shunji Shinohaea, Shiga (JP); Katsumi Koike, Shiga (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/362,922

(22) PCT Filed: Aug. 29, 2001

(86) PCT No.: PCT/JP01/07410

§ 371 (c)(1), (2), (4) Date: Feb. 27, 2003

(87) PCT Pub. No.: WO02/17954

PCT Pub. Date: Mar. 7, 2002

(65) Prior Publication Data

US 2003/0191120 A1    Oct. 9, 2003

(30) Foreign Application Priority Data

Aug. 31, 2000    (JP) ............................. 2000-262618

(51) Int. Cl.
    *A01N 43/82*    (2006.01)
(52) U.S. Cl. .................... 514/360; 514/359
(58) Field of Classification Search .................. 514/18, 514/21, 567, 360
See application file for complete search history.

(56) References Cited

U.S. PATENT DOCUMENTS

| | | | |
|---|---|---|---|
| 4,045,556 A | 8/1977 | Schwertner et al. | |
| 4,100,152 A | 7/1978 | Fujino et al. | |
| 4,386,073 Y | 5/1983 | Kisfaludy et al. | |
| 5,118,670 A * | 6/1992 | Wurtman et al. | 514/18 |
| 6,319,902 B1 * | 11/2001 | Sugawara et al. | 514/19 |

FOREIGN PATENT DOCUMENTS

| | | |
|---|---|---|
| EP | 0123444 A1 | 10/1984 |
| EP | 0225796 A2 | 6/1987 |
| EP | 0373904 A1 | 6/1990 |
| EP | 373904 A1 | 6/1990 |
| EP | 0384380 A2 | 8/1990 |
| EP | 0933379 A1 | 8/1999 |
| EP | 933379 A1 | 8/1999 |
| GB | 1519636 | 8/1978 |
| GB | 2161486 A | 1/1986 |
| JP | 60023326 A2 | 2/1985 |
| JP | 61027982 A | 2/1986 |
| JP | 62234029 A | 10/1987 |
| WO | WO 96/11209 A1 | 4/1996 |

OTHER PUBLICATIONS

Suzuki et al., J. Med. Chem., vol. 33, pp. 2130-2137 (1990).
Ogasawara et al., Biomedical Research, vol. 14, No. 5, pp. 317-328 (1993).
Oka, et al., Arzneim-Forsch./Drug Res., vol. 39 (I), No. 3, pp. 297-303 (1989).
Matsushita, et al., European Journal of Pharmacology, vol. 276, pp. 177-182 (1995).
Miyamoto et al., European Journal of Pharmacology, vol. 271, pp. 357-366 (1994).
Miwa et al., European Journal of Pharmacology, vol. 277, pp. 63-69 (1995).
Ogata et al., Journal of the Neurological Sciences, vol. 159, pp. 135-139, (1998).
Matsuura et al., Brain Research, vol. 733, pp. 101-104, (1996).
Shiozaki et al., Psychopharmacology, vol. 147, pp. 90-95 (1999).
Elsevier, Amsterdam-New York-Oxford, Design of prodrugs, pp. 7-24, (1985).
Hsiao et al., Synthetic Communications, vol. 20, No. 22, pp. 3507-3517 (1990).

(Continued)

*Primary Examiner*—Ardin H. Marschel
*Assistant Examiner*—Amy Lewis
(74) *Attorney, Agent, or Firm*—Birch, Stewart, Kolasch & Birch, LLP (57) ABSTRACT

A compound represented by the formula:

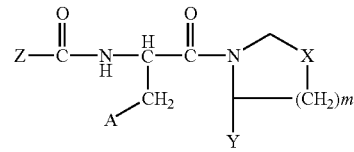

wherein A is thiazolyl or the like, X is a bond or the like, m is an integer of 0 to 4, Y is optionally substituted alkyl or the like, Z is a substituent represented by the formula:

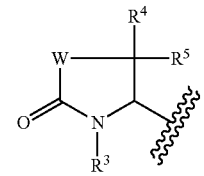

wherein $R^3$ is hydrogen atom or the like, $R^4$ and $R^5$ are each independently hydrogen atom or the like, W is —$(CH_2)_n$— (n is 0, 1, 2 or 3) or the like, a prodrug thereof, its pharmaceutically acceptable salt, or its solvate is useful as a composition for prevention or treatment of Parkinson's disease.

3 Claims, 4 Drawing Sheets

OTHER PUBLICATIONS

Paquette et al., Tetrahedron, vol. 27, pp. 2599-2607, (1971).
"The Japanese Journal of Pharmacology" p. 371, (Mar. 22-25, 1992).
Fukuchi et al., Arzneim-Forsch./Drug Res. vol. 48, No. (I), pp. 353-359 (1998).
Renming et al., European Journal of Pharmacology, vol. 223, pp. 185-192 (1992).
Kabayama et al., Brain Research, vol. 372, pp. 394-399 (1986).
Ogata, Akihiko, et al. J. Neurol. Sci., vol. 159, No. 2, pp. 135-139, 1998.

* cited by examiner

ANTIPARKINSONISM DRUGS

This application is the national phase under 35 U.S.C. § 371 of PCT International Application No. PCT/JP01/07410 which has an International filing date of Aug. 29, 2001, which designated the United States of America.

TECHNICAL FIELD

This present invention relates to an orally administrable composition for treatment or prevention of Parkinson's disease containing thyrotropin releasing hormone (thyrotropin releasing hormone; it is abbreviated as "TRH" hereafter) or its derivatives, especially a composition for treatment or prevention of Parkinson's disease exhibiting synergistic effect in combination with L-DOPA.

BACKGROUND ART

Predominant symptom of Parkinson's disease, a neurodegenerative disorder, is extrapyramidal dysfunction resulted from dopamine depletion in the basal ganglia following degenaration of nigrostriatal projection. Due to apparent therapeutic potentials of dopamine replacement, combined application of L-DOPA (levodopa, a dopamine precursor) and dopaminergic agents has been a major strategy in the treatment for Parkinson's disease. Therapeutic drugs for Parkinson's disease launched or on the development include L-DOPA, dopamine agonists, dopamine release enhancers (amantadine), anti-cholinergic drugs, L-DOPA metabolic inhibitors (MAO-B, COMT inhibitors) and norepinephrine precursors. The order of priority for using these drugs is: (amantadine and anti-cholinergic drugs), dopamine agonists and (L-DOPA, or L-DOPA+ MAO-B, COMT inhibitors). L-DOPA is the most popular drug, but its long-term application leads to loss of drug efficacy such as "wearing-off" and "on-off" and the onset of dyskinesia. Therefore, the dosage of L-DOPA should be as low as possible through combined application with other drugs. In addition, since L-DOPA is an oral agent, considering the "QOL" of patients, co-administrated drugs are desirable to be of the same type.

L-pyroglutamyl-L-histidyl-L-prolinamide (p-Glu-His-Pro-NH$_2$) known as TRH (thyrotropin releasing hormone) is a hormone discovered in the hypothalamus and consisting of 3 amino acid residues. This hormone is suggested to act through TRH receptors. TRH is known not only to promote the secretion of TSH (tyrotoropin stimulating hormone) and prolactin, but also to have cerebral nerve activation (stimulation of motor function and the like), effects on sympathetic nervous system (elevation of blood pressure, stimulation of respiratory and the like), effects on spinal function (stimulation of spinal motoneuron and the like), effects on central nervous system (antidepressant activity and the like) and peripheral actions (suppression of gastric acid secretion, stimulation of glucagon secretion and the like). Having such various activities, TRH has been investigated for the clinical use, and is being used as an intravenous injection for treating spinocerebellar degeneration for purposes of improvement of motility disturbance and cognitive disturbance accompanied by brain functional disturbance (Sofue, Kanazawa, Ogawa, "Neuropeptide" '91, Medicalreview).

The structure of TRH derivatives with more enhanced activities for central nervous system generally consists of 3 amino acid residues as well as TRH or their derivatives. Most of the derivatives have a molecular weight of about 370 to 430. For example, they are described in the following documents: J. Med. Chem, 33, 2130–2137 (1990) and JP Laid-Open (Kokai) No. 86/33197 (e.g.: Taltirelin; TA-0910); Biomedical Research 14 (5) 317–328 (1993) and ZA7505956 (montirelin; CG3703); Arzneim.-Forsch/Drug Res., 39, 297–303 (1989) and JP Laid-Open (Kokai) No. 81/8354 (posatirelin; RGH2202); Eur. J. Pharmacol. 276, 177–182 (1995) and JP Laid-Open (Kokai) No. 91/236397 (e.g.: JTP-2942); JP Patent-Publication (Kokoku) No. 90/36574 (e.g.:1-methyl-L-4,5-dihydroorotyl-L-histidyl-L-prolinamide): JP Laid-Open (Kokai) No. 77/116465 (e.g.: 2,3,4, 5-tetrahydro-2-oxo-L-5-furancarbonyl-L-histidyl-L-prolinamide); JP Patent-Publication (Kokoku) No. 91/236397 (e.g.: (1S,2R)-2-methyl-4-oxocyclopentylcarbonyl-L-histidyl-L-prolinamide); JP Patent-Publication (Kokoku) No. 84/36612 (e.g.: orotyl-L-histidyl-L-prolinamide); Eur. J. Pharmacol., 271, 357 (1994) (e.g.: TRH-SR); JP Laid-Open (Kokai) No. 77/3080; Eur. J. Pharmacol. 277, 63–69 (1995) and JP Laid-Open (Kokai) No. 85/27982 (e.g.: azetirelin; YM14673); JP Laid-Open (Kokai) No. 85/23326 (e.g.: DN1417); JP Laid-Open (Kokai) No. 87/234029; JP Laid-Open (Kokai) No. 81/8354; WO96/11209; WO98/08867, and the like. Compounds exemplified in examples in the present invention are described in WO98/08867.

It is described in "Journal of the Neurological Science 159 (1998) 135–139" that an intraperitoneal injection of TRH-SH (sustained release microspheres of TRH, Takeda Chemical Industries, Ltd.) increased striatal dopamine levels in Japanese encephalitis virus (JEV)-induced post-encephalitic parkinsonism mice compared with untreated group. However, it is described in the paper that mechanisms underlying post-encephalitic parkinsonism were different from that for Parkinson's disease. Further it is described that TRH-SH may be used as a supportive drug of L-DOPA, without mentioning the increase of L-DOPA activities or the synergistic action in combination use. Furthermore, TRH-SH is essentially a drug for injection and the possibility of oral administration is not mentioned there.

DISCLOSURE OF INVENTION

The present invention provides an orally administrable composition for treatment or prevention of Parkinson's disease.

The inventors of the present invention examined on the spontaneous locomotor activity of mice injected intracerebroventricularly with a monoaminergic toxin, 6-OHDA or with MPTP, or on the cataleptic responses of mice pretreated with a monoamine-depleting drug, reserpine and found that TRH or TRH derivatives can be an orally administrable composition for treatment or prevention of Parkinson's disease and especially that they exhibits a remarkable effect in combination with L-DOPA.

The inventors of the present invention accomplished the present invention as follows.

The present invention relates to I) a pharmaceutical composition for prevention or treatment of Parkinson's disease, which contains as an active ingredient TRH or a TRH derivative.

In more detail, the present invention relates to the following II) to XXVIII).

II) A pharmaceutical composition enhancing an L-DOPA activity, which contains as an active ingredient TRH or a TRH derivative.

III) A pharmaceutical composition enhancing an L-DOPA activity as described in II), which is for prevention or treatment of Parkinson disease.

IV) A pharmaceutical composition as described in any one of I) to III), wherein TRH or a TRH derivative is compound represented by formula (I):

(I)

wherein $A^0$ is thiazolyl, imidazolyl, or alkyl, X is a bond, oxygen atom, or sulfur atom, m is an integer of 0 to 4, Y is optionally substituted alkyl, optionally substituted carboxy, cyano, or a substituent represented by the formula:

wherein $R^1$ and $R^2$ are independently hydrogen atom, or optionally substituted alkyl, or $R^1$ and $R^2$ taken together with the adjacent nitrogen may form a non-aromatic heterocyclic ring which may contain oxygen, nitrogen, or sulfur and may be substituted, $Z^0$ is a substituent represented by the formula:

wherein $R^3$ is hydrogen atom, optionally substituted alkyl, optionally substituted carboxy, or optionally substituted acyl, $R^4$ and $R^5$ are each independently hydrogen atom or optionally substituted alkyl, and W is —(CH$_2$)n—wherein n is 0, 1, 2, or 3, oxygen atom, sulfur atom, or optionally substituted imino, or a substituent represented by the formula:

wherein $R^6$ is hydrogen atom or lower alkyl, a broken line ( . . . ) represents the presence or absence of a bond or a substituent represented by the formula:

wherein $R^7$ is hydrogen atom or lower alkyl or a substituent represented by the formula:

or a substituent represented by the formula:

wherein $R^8$ is hydrogen atom or lower alkyl, provided that nitrogen atom in thiazolyl ring may be a quaternary nitrogen atom which is formed with optionally substituted alkyl or alkenyl, its prodrug, their pharmaceutically acceptable salt, or solvate thereof.

V) A pharmaceutical composition as described in any one of I) to III), wherein TRH or a TRH derivative is a compound represented by formula (II):

(II)

wherein X, Y, $Z^0$, m are defined as above, A is 4-thiazolyl, or 5-thiazolyl, provided that nitrogen atom in thiazolyl ring may be a quaternary nitrogen atom which is formed with optionally substituted alkyl or alkenyl, its prodrug, their pharmaceutically acceptable salt, or solvate thereof.

VI) A pharmaceutical composition as described in any one of I) to III), wherein TRH or a TRH derivative is a compound represented by formula (III):

(III)

wherein A, X, Y, m are defined as above, Z is a substituent represented by the formula:

wherein R³ is hydrogen atom, optionally substituted alkyl, optionally substituted carboxy, or optionally substituted acyl, R⁴ and R⁵ are each independently hydrogen atom or optionally substituted alkyl, and W is —(CH₂)n— wherein n is 0, 1, 2, or 3, oxygen atom, sulfur atom, or optionally substituted imino, or a substituent represented by the formula:

provided that nitrogen atom in thiazolyl ring may be a quaternary nitrogen atom which is formed with optionally substituted alkyl or alkenyl, its prodrug, their pharmaceutically acceptable salt, or solvate thereof.

VII) A pharmaceutical composition as described in any one of I) to III), wherein TRH or a TRH derivative is a compound represented by formula (IV):

(IV)

wherein X, Y, Z, m are defined above, provided that nitrogen atom in thiazolyl ring may be a quaternary nitrogen atom which is formed with optionally substituted alkyl or alkenyl, its prodrug, their pharmaceutically acceptable salt, or solvate thereof.

VIII) A pharmaceutical composition as described in any one of I) to III), wherein TRH or a TRH derivative is a compound represented by formula (V):

(V)

wherein X, Y, Z, m are defined above, provided that nitrogen atom in thiazolyl ring may be a quaternary nitrogen atom which is formed with optionally substituted alkyl or alkenyl, its prodrug, their pharmaceutically acceptable salt, or solvate thereof.

IX) A pharmaceutical composition as described in any one of I) to III), wherein TRH or a TRH derivative is a compound represented by formula (VI):

(VI)

wherein W, X, Y, m, R³, R⁴, R⁵ are defined as above.

its prodrug, their pharmaceutically acceptable salt, or solvate thereof.

X) A pharmaceutical composition as described in any one of I) to III), wherein TRH or a TRH derivative is a compound represented by formula (VII):

(VII)

wherein Y is defined as above, its prodrug, their pharmaceutically acceptable salt, or solvate thereof.

XI) A pharmaceutical composition as described in any one of I) to III), wherein TRH or a TRH derivative is a compound represented by formula (VIII):

(VIII)

wherein Y is defined as above, its prodrug, their pharmaceutically acceptable salt, or solvate thereof.

XII) A pharmaceutical composition as described in any one of I) to III), wherein TRH or a TRH derivative is a compound represented by formula (IX):

(IX)

its prodrug, their pharmaceutically acceptable salt, or solvate thereof.

XIII) A pharmaceutical composition as described in any one of IV) to IX), containing as an active ingredient a compound, its prodrug, their pharmaceutically acceptable salt, or solvate thereof, wherein m is 1 or 2, provided that X is not a bond when m is 1.

XIV) A pharmaceutical composition as described in any one of IV) to IX), containing as an active ingredient a compound, its prodrug, their pharmaceutically acceptable salt, or solvate thereof, wherein X is sulfur atom, m is 1, and Y is optionally substituted alkyl, optionally substituted carboxy, or optionally substituted carbamoyl.

XV) A pharmaceutical composition as described in any one of IV) to IX), containing as an active ingredient a compound, its prodrug, their pharmaceutically acceptable salt, or solvate thereof, wherein X is a bond, m is 2 or 3, and Y is optionally substituted alkyl, optionally substituted carboxy, or optionally substituted carbamoyl.

XVI) A pharmaceutical composition as described in any one of I) to XV), which is an oral agent.

XVII) A pharmaceutical composition as described in any one of I) to XVI), which exhibits a synergic effect in combination with L-DOPA XVIII) A pharmaceutical composition as described in XVII), which exhibits a synergic effect in combination with an ineffective amount of L-DOPA.

XIX) A method for treating a mammal, including a human, to alleviate the pathological effects of Parkinson's disease, which comprises administration to said mammal of TRH or a TRH derivative as described in any one of I) to XV) in a pharmaceutically effective amount.

XX) A method for enhancing an L-DOPA activity, which comprises administration to a mammal, including a human, of TRH or a TRH derivative as described in any one of I) to XV) in a pharmaceutically effective amount.

XXI) Use of TRH or a TRH derivative of any one of I) to XV) for preparation of a pharmaceutical composition for treating Parkinson's disease.

XXII) Use of TRH or a TRH derivative of any one of I) to XV) for preparation of a pharmaceutical composition for enhancing an L-DOPA activity.

XXIII) A pharmaceutical composition for increase of the spontaneous locomotor activity which contains as an active ingredient TRH or a TRH derivative.

XXIV) A pharmaceutical composition for amelioration of dyskinesia which contains as an active ingredient TRH or a TRH derivative.

XXV) A method for increasing the spontaneous locomotor activity, which comprises administration to a mammal, including a human, of TRH or a TRH derivative as described in any one of I) to XV) in a pharmaceutically effective amount.

XXVI) A method for ameliorating dyskinesia, which comprises administration to a mammal, including a human, of TRH or a TRH derivative as described in any one of I) to

XV) in a pharmaceutically effective amount.

XXVII) Use of TRH or a TRH derivative of any one of I) to XV) for preparation of a pharmaceutical composition for increasing the spontaneous locomotor activity.

XXVIII) Use of TRH or a TRH derivative of any one of I) to XV) for preparation of a pharmaceutical composition for ameliorating dyskinesia.

In the present specification, the term "TRH" means L-pyroglutamyl-L-histidyl-L-prolinamide (p-Glu-His-Pro-NH$_2$) known as a thyrotropin releasing hormone.

The term "TRH derivatives" herein used includes compounds having activities of TRH hormone, which consists of 3 amino acid residues as well as TRH or their derivatives and have a molecular weight of about 370 to 430. For example, these compounds are described in J. Med. Chem, 33, 2130–2137 (1990) and JP Laid-Open (Kokai) No. 86/33197 (e.g.: Taltirelin; TA-0910); Biomedical Research 14 (5) 317–328 (1993) and ZA7505956 (montirelin; CG3703); Arzneim.-Forsch/Drug Res., 39, 297–303 (1989) and JP Laid-Open (Kokai) No. 81/8354 (posatirelin; RGH2202); Eur. J. Pharmacol. 276, 177–182 (1995) and JP Laid-Open (Kokai) No. 91/236397 (e.g.: JTP-2942); JP Patent-Publication (Kokoku) No. 90/36574 (e.g.:1-methyl-L-4,5- dihydroorotyl-L-histidyl-L-prolinamide); JP Laid-Open (Kokai) No. 77/116465 (e.g.: 2,3,4,5-tetrahydro-2-oxo-L-5-furancarbonyl-L-histidyl-L-prolinamide); JP Patent-Publication (Kokoku) No. 91/236397 (e.g.: (1S,2R)-2-methyl-4-oxocyclopentylcarbonyl-L-histidyl-L-prolinamide); JP Patent-Publication (Kokoku) No. 84/36612 (e.g.: orotyl-L-histidyl-L-prolinamide); Eur. J. Pharmacol., 271, 357 (1994) (e.g.: TRH-SR); JP Laid-Open (Kokai) No. 77/3080; Eur. J. Pharmacol. 277, 63–69 (1995) and JP Laid-Open (Kokai) No. 85/27982 (e.g.: azetirelin; YM14673); JP Laid-Open (Kokai) No. 85/23326 (e.g.: DN1417); JP Laid-Open (Kokai) No. 87/234029; JP Laid-Open (Kokai) No. 81/8354; WO96/11209; WO98/08867, and the like. Concretely, the following compounds are exemplified.

The term "A composition enhancing a L-DOPA activity" herein used includes an agent enhancing the effect for treatment in single administration of L-DOPA by combined medication. Especially, preferable are agents exhibiting a synergistic effect in combined medication compared with single administration of L-DOPA. More preferable are agents exhibiting the effect for treatment in combination with an amount of L-DOPA which does not exhibit the effect for treatment in single administration. For example, the composition is useful for treatment of diseases using L-DOPA. That is, the composition means agents enhancing an L-DOPA activity in combined medication for diseases for which L-DOPA is used or will be. Such diseases include Parkinson's disease or Parkinson's syndrome. Especially, Parkinson's disease is preferable.

The term "a composition for increase of the spontaneous locomotor activity" herein used includes an agent which can increase the spontaneous locomotor activity.

The term "a composition for amelioration of dyskinesia" herein used includes an agent which can ameliorate dyskinesia caused by neurotoxin, virus, cerebrovascular disorder or something else.

The meaning of each term is defined as follow. In the present specification, each term employed alone or in combination with other terms is used in the same meaning.

The term "halogen" herein used means fluoro, chloro, bromo, and iodo.

The term "alkyl" herein used includes $C_1$–$C_6$ straight or branched chain alkyl and $C_3$–$C_6$ cyclic alkyl. Preferably, $C_1$–$C_6$ straight or branched chain alkyl is exemplified. Further preferably, $C_1$–$C_3$ straight or branched chain alkyl is exemplified. Examples of alkyl are methyl, ethyl, n-propyl, isopropyl, n-butyl, isobutyl, sec-butyl, tert-butyl, cyclopropyl, cyclopentyl, cyclohexyl, and the like.

Especially, the term "lower alkyl" herein used includes $C_1$–$C_3$ straight or branched chain alkyl. Examples of lower alkyl are methyl, ethyl, n-propyl, isopropyl, and the like.

The term "alkenyl" herein used includes $C_2$–$C_8$ straight or branched chain alkenyl. Preferably, $C_3$–$C_6$ straight or branched chain alkenyl is exemplified. Further preferably, $C_2$–$C_5$ straight or branched chain alkenyl is exemplified. Examples of alkenyl are n-propenyl, n-butenyl, n-hexenyl, and the like.

The term "aryl" herein used includes monocyclic or condensed ring aromatic hydrocarbons. Preferably, monocyclic aromatic hydrocarbons are exemplified. Examples of aryl are phenyl, naphthyl, and the like.

The term "heteroaryl" includes a 5 to 6 membered aromatic heterocyclic group which contains one or more hetero atoms selected from the group consisting of nitrogen, oxygen and sulfur atoms in the ring, may be fused with a carbocyclic ring or an other heterocyclic ring, and may be substituted at any possible position. Examples of the heteroaryl are pyrrolyl (e.g., 1-pyrrolyl), indolyl (e.g., 2-indolyl), carbazolyl (e.g., 3-carbazolyl), imidazolyl (e.g., 4-imidazolyl), pyrazolyl (e.g., 1-pyrazolyl), benzimidazolyl (e.g., 2-benzimidazolyl), indazolyl (e.g., 3-indazolyl), indolizinyl (e.g., 6-indolizinyl), pyridyl (e.g., 4-pyridyl), quinolyl (e.g., 5-quinolyl), isoquinolyl (e.g., 3-isoquinolyl), acridinyl (e.g., 1-acridinyl), phenanthridinyl (e.g., 2-phenanthridinyl), pyridazinyl (e.g., 3-pyridazinyl), pyrimidinyl (e.g., 4-pyrimidinyl), pyrazinyl (e.g., 2-pyrazinyl), cinnolinyl (e.g., 3-cinnolinyl), phthalazinyl (e.g., 2-phthalazinyl), quinazolinyl (e.g., 2-quinazolinyl), isoxazolyl (e.g., 3-isoxazolyl), benzisoxazolyl (e.g., 3-benzisoxazolyl), oxazolyl (e.g., 2-oxazolyl), benzoxazolyl (e.g., 2-benzoxazolyl), benzoxadiazolyl (e.g., 4-benzoxadiazolyl), isothiazolyl (e.g., 3-isothiazolyl), benzisothiazolyl (e.g., 2-benzisothiazolyl), thiazolyl (e.g., 2-thiazolyl), benzothiazolyl (e.g., 2-benzothiazolyl), furyl (e.g., 3-furyl), benzofuryl (e.g., 3-benzofuryl), thienyl (e.g., 2-thienyl), benzothienyl (e.g., 2-benzothienyl), tetrazolyl, and the like.

The term "non-aromatic heterocyclic group" herein used means a 5 to 7 membered non-aromatic heterocyclic group which contains one or more hetero atoms selected from the group consisting of oxygen, sulfur and nitrogen atoms in the ring, and may be substituted at any possible position. Examples of the non-aromatic heterocyclic group are morpholino, piperidino, 1-pyrrolidinyl, 2-pyrroline-3-yl, and the like.

The term "acyl" herein used includes alkanoyl of which alkyl part is the above mentioned "alkyl" and aroyl of which aryl part is the above mentioned "aryl". Examples of acyl are acetyl, benzoyl, and the like.

The term "alkyloxy" herein used includes alkyloxy of which alkyl part is the above mentioned "alkyl". Examples of alkyloxy are methyloxy, ethyloxy, n-propyloxy, isopropyloxy, n-butyloxy, isobutyloxy, sec-butyloxy, tert-butyloxy, and the like.

The term "optionally substituted alkyl" for $R^1$ and $R^2$ herein used includes the above mentioned "alkyl" which is optionally substituted at any possible position with one or more substituents, for example, hydroxy, alkyloxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, carbamoyl, $C_1$–$C_{20}$ alkyloxycarbonyl (e.g., methoxycarbonyl, isopropyloxycarbonyl, tetradecanyloxycarbonyl, and pentadecanyloxycarbonyl), aryloxycarbonyl (e.g., phenyloxycarbonyl), nitro, cyano, $SO_pR^A$ (p is an integer of 1 to 3, and $R^A$ is hydrogen or alkyl), $PO(OH)_2$ or $PO(O)OH$ which is optionally substituted with alkyl, substituted or unsubstituted amino (e.g., methylamino, dimethylamino, and carbamoylamino), optionally substituted aryl (e.g., phenyl and tolyl), optionally substituted heteroaryl, an optionally substituted non-aromatic-heterocyclic group, aryloxy, acyloxy, acyloxycarbonyl, alkylcarbonyl, arylcarbonyl, non-aromatic heterocyclic carbonyl, hydrazino, hydroxyamino, alkyloxyamino, and formyl. Examples of optionally substituted alkyl are methyl, ethyl, n-propyl, isopropyl, n-butyl, isobutyl, sec-butyl, tert-butyl, cyclopropyl, cyclopentyl, cyclohexyl, benzyl, isopropyloxycarbonylmethyl, tetradecanyloxycarbonylmethyl, pentadecanyloxycarbonylmethyl, and the like. As the preferred substituent, $C_1$–$C_{20}$ alkyloxycarbonyl and phenyl are exemplified.

The term "optionally substituted alkyl" for Y, $R^3$, $R^4$, and $R^5$ herein used includes the above mentioned "alkyl" which is optionally substituted at any possible position with one or more substituents, for example, hydroxy, alkyloxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, carbamoyl, alkyloxycarbonyl (e.g., methoxycarbonyl and ethoxycarbonyl), aryloxycarbonyl (e.g., phenyloxycarbonyl), nitro, cyano, $SO_pR^A$ (p is an integer of 1 to 3, and $R^A$ is hydrogen or alkyl), $PO(OH)_2$ or $PO(O)OH$ which is optionally substituted with alkyl, substituted or unsubstituted amino (e.g., methylamino, dimethylamino, and carbamoylamino), optionally substituted aryl (e.g., phenyl and tolyl), optionally substituted heteroaryl, an optionally substituted non-aromatic-heterocyclic group, aryloxy, acyloxy, acyloxycarbonyl, alkylcarbonyl, non-aromatic heterocyclic carbonyl, heterocyclic imino, hydrazino, hydroxyamino, alkyloxyamino, and formyl. For example, methyl, ethyl, n-propyl, isopropyl, n-butyl, isobutyl, sec-butyl, tert-butyl, cyclopropyl, cyclopentyl, cyclohexyl, benzyl, hydroxymethyl, tert-butylcarbonyloxymethyl, morpholinomethyl, piperidinomethyl, N-methyl-1-piperazinylmethyl, ethylcarbonylmethyl, morpholinocarbonylmethyl, acetyloxymethyl, and the like are exemplified. As a preferable substituent, phenyl, hydroxy, alkylcarbonyloxy, morpholino, piperidino, N-alkyl-substituted piperazinyl, alkylcarbonyl, morpholinocarbonyl, acyloxy are exemplified.

The term "optionally substituted alkyl" for nitrogen in the thiazolyl ring herein used includes $C_1$–$C_3$ straight or branched chain alkyl which is optionally substituted with phenyl optionally substituted with halogen or alkyl. For example, methyl, ethyl, n-propyl, n-butyl, benzyl, 4-methylbenzyl are exemplified.

The terms "optionally substituted aryl", "optionally substituted heteroaryl", and "an optionally substituted non-aromatic heterocyclic group" herein used include the above mentioned "aryl", "heteroaryl", and "a non-aromatic heterocyclic group", respectively, which are optionally substituted with one or more substituents, for example, hydroxy, alkyloxy (e.g., methoxy and ethoxy), mercapto, alkylthio (e.g., methylthio), halogen (e.g., fluoro, chloro, bromo, and iodo), carboxy, alkyloxycarbonyl (e.g., methoxycarbonyl and ethoxycarbonyl), nitro, cyano, haloalkyl (e.g., trifluoromethyl), aryloxy (e.g., phenyloxy), substituted or unsubstituted amino (e.g., methylamino, dimethylamino, diethylamino, and bezylideneamino), guanizino, alkyl (e.g., methyl, ethyl, n-propyl, isopropyl, n-butyl, isobutyl, sec-butyl, tert-butyl, n-pentyl, isopentyl, neo-pentyl, tert-pentyl, cyclopropyl, cyclobutyl, and cyclopentyl), alkenyl (e.g., vinyl and propenyl), alkynyl (e.g., ethynyl and phenylethynyl), alkanoyl (e.g., formyl, acetyl and propionyl), acyloxy (e.g., acetyloxy) acylamino, alkylsulfonyl (e.g., methylsulfonyl), phenyl, benzyl, an azo group (e.g., phenylazo), optionally substituted heteroaryl (e.g., 3-pyridyl), optionally substituted ureido (e.g., ureido and phenylureido), and the like.

The substituents for "optionally substituted carboxy" of Y are, for example, straight or branched chain $C_1$–$C_{20}$ alkyl, cyclic $C_3$–$C_8$ alkyl, and aryl. Further, these alkyl and aryl are optionally substituted with one or more substituents which are exemplified as those for the above "optionally substituted alkyl" and "optionally substituted aryl". Examples of the "optionally substituted carboxy" are carboxy, alkyloxycarbonyl and aryloxycarbonyl, for example, methoxycarbonyl, isopropyloxycarbonyl, hexyloxycarbonyl, decyloxycarbonyl, phenyloxycarbonyl, tetradecyloxycarbonyl, icosanyloxycarbonyl, phenoxymethylcarbonyl, benzyloxycarbonyl, tolyloxycarbonyl, and the like. As a preferable substituent, straight or branched chain $C_1$–$C_{20}$ alkyl and benzyl are exemplified.

The substituents for "optionally substituted carbamoyl" of Y are, for example, straight or branched chain $C_1$–$C_6$, alkyl (e.g., methyl, ethyl, n-propyl, and isopropyl). Further, this alkyl is optionally substituted with one or more substituents which are exemplified as those for the above "optionally substituted alkyl". Examples of the "optionally substituted carbamoyl" are carbamoyl, methylcarbamoyl, ethylcarbamoyl, n-propylcarbamoyl, methylethylcarbamoyl, benzylcarbamoyl, isopropyloxycarbonylmethylcarbamoyl, tetradecanyloxycarbonylmethylcarbamoyl, benzyloxycarbonylmethylcarbamoyl, acetyloxymethylcarbamoyl, acetylcarbamoyl, and the like. As a preferable substituent, $C_1$–$C_{20}$ alkyloxycarbonylalkyl and acyloxyalkyl are exemplified.

The substituents for "optionally substituted carboxy" of $R^3$ are, for example, the above mentioned "optionally substituted alkyl" and "optionally substituted aryl". Examples of the "optionally substituted carboxy" are carboxy, alkyloxycarbonyl, and aryloxycarbonyl, for example, methoxycarbonyl, ethoxycarbonyl, phenoxycarbonyl, phenyloxymethylcarbonyl, tolyloxycarbonyl, and the like.

The term "optionally substituted acyl" herein used includes alkanoyl of which alkyl part is the above mentioned "optionally substituted alkyl" and aroyl of which aryl part is the above mentioned "optionally substituted aryl". Examples of the "optionally substituted acyl" are toluoyl and the like.

The term "optionally substituted imino" herein used includes the imino which is optionally substituted with the above mentioned "optionally substituted lower alkyl", "optionally substituted aryl", alkyloxycarbonyl, and the like.

BEST MODE FOR CARRYING OUT THE INVENTION

TRH or TRH derivatives useful for treatment or prevention of Parkinson's disease can be synthesized in accordance with known methods described in WO98/08867 and the like.

The effect for treatment of Parkinson's disease can be confirmed based on examination on the spontaneous locomotor activity of mice injected intracerebroventricularly with a monoaminergic toxin, 6-OHDA, or of MPTP-treated mice, and examinations on cataleptic responses of mice pre-treated with a monoamine-depleting drug, reserpine (Matsuura, K. et al. (1996) Brain Res. 733 p101–104, Shiozaki, S. et al. (1999) Psychopharmacology 147 p90–95).

The term "the solvates" herein used includes, for example, solvates with organic solvents and/or hydrates. In case of forming a hydrate, a questioned compound may be coordinated with a suitable number of water molecules.

The term "the compounds of this invention" herein used includes pharmaceutically acceptable salts or hydrates of the compounds. For example, salts with alkali metals (e.g., lithium, sodium, and potassium), alkaline earth metals (e.g., magnesium and calcium), ammonium, organic bases, amino acids, mineral acids (e.g., hydrochloric acid, hydrobromic acid, phosphoric acid, and sulfuric acid), or organic acids (e.g., acetic acid, citric acid, maleic acid, fumaric acid, benzenesulfonic acid, and p-toluenesulfonic acid) are exemplified. These salts can be formed by the usual method.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example. Design of Prodrugs, Elsevier, Amsterdam, 1985. For instance, prodrugs, such as an ester derivative which is prepared by reacting a basal acid compound with a suitable alcohol, or an amide derivative which is prepared by reacting a basal acid compound with a suitable amine, are exemplified when the compounds according to present invention have a carboxylic group. Particularly preferred esters as prodrugs are methyl ester, ethyl ester, n-propyl ester, isopropyl ester, n-butyl ester, isobutyl ester, tert-butyl ester, morpholinoethyl ester, and N,N-diethylglycolamido ester, and the like. For instance, prodrugs such as an acyloxy derivative which is prepared by reacting a basal hydroxy compound with a suitable acyl halide or a suitable acid anhydride are exemplified when the compounds according to present invention have a hydroxy group. Particularly preferred acyloxy derivatives as prodrugs —$OCOC_2H_5$, —OCO(t-Bu), —$OCOC_{15}H_{31}$, —OCO(m-COONa-Ph), —$OCOCH_2CH_2COONa$, —$OCOCH(NH_2)CH_3$, —$OCOCH_2N(CH_3)_2$, and the like. For instance, prodrugs such as an amide derivative which is prepared by reacting a basal amino compound with a suitable acid halide or a suitable acid anhydride are exemplified when the compounds according to present invention have an amino group. Particularly preferred amide as prodrugs are —$NHCO(CH_2)_{20}CH_3$, —$NHCOCH(NH_2)CH_3$, and the like.

The compound of the present invention is not restricted to any particular isomers but includes all possible isomers and racemic modifications, if there is no proviso.

The compound of the present invention has an excellent effect for treating Parkinson's disease, as described in the following test example. Especially, the effect is remarkable in combination with L-DOPA.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier. Taking QOL of subjects into account, oral administration is preferred.

The dosage varies with the conditions of the patients, administration route, their age, and body weight. In the case of oral administration, the dosage can generally be between 0.1 to 100 mg/kg/day, and preferably 0.1 to 20 mg/kg/day for adult.

The following examples are provided to further illustrate the present invention and are not to be construed as limiting the scope thereof.

Abbreviations described below are used in the following examples.
Me: methyl
THF: tetrahydrofuran
DCC: 1,3-dicyclohexylcarbodiimide
p.o.: oral administration
i.p.: intraperitoneal administration
6-OHDA: 6-hydroxydopamine
MPTP: 1-methyl-4-phenyl-1,2,3,6-tetrahydropyridine
DA: dopamine

EXAMPLE

Example 1

Preparation of the Compound Represented by Formula (IX)

(Process 1)

To N-(tert-butoxycarbonyl)-3-(4-thiazolyl)-L-alanine (1, 21.79 g, 80 mmol) prepared in accordance with a reference (Synth. Commun., 20, 3507 (1990)) was added trifluoroacetic acid (80 ml) and stirred in an ice bath for 2.5 h. To the reaction mixture was added p-tolunesulfonic acid hydrate (15.22 g, 80 mmol), and then the mixture was stirred at room temperature for 30 min and evaporated in reduced pressure. To the obtained residue was added water and methanol, and the mixture was concentrated in reduce pressure to remove excess trifluoroacetic acid. To the obtained residue was added ether and the precipitated crystal was filtrated to give the product (2) 29.8 g (quantitative).

NMR(CD$_3$OD):9.01(1H, d, J=1.8 Hz),7.70 (2H, m),7.46 (1H, d, J=1.8 Hz), 7.23(2H, m), 4.38(1H, dd, J=4.8 and 7.6 Hz), 3.45(2H, m), 2.37(3H, s).

(Process 2)

To a solution of the compound (2) 38.85 g (112.8 mmol) in ethanol (200 ml)—THF (600 ml) was added with stirring at room temperature diphenyldiazomethane (39 g, 201 mmol) in divisions over 30 min. After the reaction mixture was stirred at room temperature for 1 h, diphenyldiazomethane (10 g, 51.5 mmol) was added and the mixture was stirred for 1 h. To the reaction mixture was added acetic acid (0.1 ml) to decompose the excess reagents, and the mixture was evaporated to remove the solvent in reduced pressure. To the obtained residue (92 g) was added ether (1 L) to crystallize the compound (3) 49.05 g (96.1%).

mp: 139–140° C.

[α]$_D$=−34.7° (c=1.006, CHCl$_3$, 23° C.)

IR(KBr)cm$^{-1}$: 1753, 1602, 1512, 1496, 1260, 1224, 1171, 1124, 1036, 1012.

NMR(CD$_3$OD):8.92(1H, d, J=2 Hz), 7.70(2H, m), 7.2–7.4(13H, m), 6.91(1H, s), 4.62 (1H, t, J=5.8 Hz), 3.47(2H, d, J=5.8 Hz), 2.36(3H, s).

Elemental analysis (C$_{26}$H$_{26}$N$_2$O$_5$S$_2$)
Calcd.: C,61.16;H,5.13;N,5.49; S,12.56.
Found: C,61.14;H,5.32;N,5.41;S,12.46.

(Process 3)

To a solution of cis-L-5-methyl-2-oxo-oxazoline-4-carboxylic acid 13.95 g (96.14 mmol), compound (3) 49.09 g (96.14 mmol), N-hydroxybezotriazole 2.6 g (19.23 mmol) and triethylamine 14.1 ml (101 mmol) in THF (1L) was added in an ice bath DCC (20.83 g, 101 mmol). After the mixture was stirred at the same temperature for 10 min, the ice bath was removed and the mixture was stirred at room temperature for 20 min. The precipitate was filtrated and the filtrate was evaporated in reduced pressure to give an oily residue (82.7 g). The residue was dissolved in ethyl acetate (700 ml) with heating to filtrate insoluble substances. The filtrate was washed successively with an aqueous sodium carbonate solution and water. To the organic layer was added methanol (20 ml), and it was dried over magnesium sulfate and concentrated to a small amount in reduced pressure. The precipitated crystal was filtrated, washed with a mixed solvent of ethyl acetate-ether (2:3) to give the compound (4) 35.69 g (79.8%). Furthermore, mother liquor was evaporated in reduced pressure and crystallization from a mixed solvent of ethyl acetate-ether gave the compound (4) 2.62 g (5.9%).

mp: 176–177° C.

$[\alpha]_D$=-39.2° (c=1.007, $CHCl_3$, 24° C.)

IR(KBr)$cm^{-1}$: 1739, 1681, 1508, 1453, 1386, 1237, 1193, 1089.

NMR($CDCl_3$):8.71(1H, d, J=1.8 Hz), 8.18(1H, d, J=7.8 Hz), 7.2–7.4(10H, m), 6.82(1H, s), 6.66(1H, d, J=1.8 Hz), 5.79(1H, s), 5.12(1H, m), 4.94(1H, m), 4.35(1H, dd, J=1.8 and 9.0 Hz), 3.40(1H, dd, J=5.7 and 15 Hz), 3.29(1H, dd, J=4.5 and 15 Hz), 1.27(3H, d, J=6.3 Hz).

Elemental analysis ($C_{24}H_{23}N_3O_5S$)

Calcd.:C,61.92;H,4.98;N,9.03;S,6.89.

Found:C,61.95;H,5.01;N,8.94;S,6.62.

(Process 4)

To the compound (4) 41.24 g (88.59 mmol) were added in an ice bath anisole (240 ml) and trifluoroacetic acid (120 ml), and the reaction mixture was stirred for 15 min. After the ice bath was removed, the mixture was stirred at room temperature for 2 h and 30 min. The reaction mixture was evaporated in reduced pressure and to the obtained oily residue was added ether (500 ml) and the mixture was powdered and filtrated. The obtained powder was dissolved with heating in a mixed solvent of water (50 ml)-methanol (300 ml) to remove insoluble substances. After the filtrate was evaporated in reduced pressure to small amount, to the resulting solution were added seed crystal and methanol and it was kept at room temperature for 3 days. The precipitated crystal was filtrated to give the product (5) 14.89 g (56.1%). The mother liquor was evaporated in reduced pressure and the residue was crystallized from a mixed solvent of methanol-ether to obtain the compound (5) 10.3 g (38%).

mp:214–215° C.

$[\alpha]_D$=-4.2° (c=0.5, $H_2O$, 22° C.)

IR(KBr)$cm^{-1}$: 1753, 1707, 1655, 1548, 1529, 1409, 1343, 1264, 1236, 1102, 1092.

NMR(DMSO-d6): 9.02(1H, d, J=1.8 Hz), 8.46(1H, d, J=7.8 Hz), 7.74(1H, s), 7.38(1H, d, J=1.8 Hz), 4.77(1H, dq, J=6.6 and 8.7 Hz), 4.66(1H, m), 4.21(1H, d, J=8.7 Hz), 3.24 (1H, dd, J=5.1 and 15 Hz), 3.13(1H, dd, J=8.4 and 15 Hz), 1.13(3H, d, J=6.6 Hz).

Elemental analysis ($C_{11}H_{13}N_3O_5S$)

Calcd.: C,44.14;H,4.38;N,14.04;S,10.71.

Found: C,43.94;H,4.478;N,14.09;S,10.58.

(Process 5)

To a suspension of compound (5) 12.1 g, (40.48 mmol) and N-hydroxy succinimide (4.66 g, 40.48 mM) in THF (242 ml) was added in an ice bath DCC (8.35 g, 40.48 mmol) and the mixture was stirred for 30 min. After the ice bath was removed, the reaction mixture was stirred at room temperature for 2 h. The obtained solution of N-hydroxy succinimide ester of the compound (5) was added at room temperature to a suspension of (R)-(+)-2-methyl pyrrolidine hydrochloride (5.42 g) prepared in accordance with a reference (Tetrahedron, 27, 2599 (1971)) and triethylamine (8.46 ml, 60.72 mmol) in THF (121 ml) and the reaction mixture was stirred at room temperature for 15 h. After the precipitated insoluble substance was removed, the filtrate was evaporated in a reduced pressure. The residue (24.6 g) was dissolved in water (150 ml) to remove insoluble substance. The filtrate was purified with a gel filtration chromatography (MCI Gel CHP-20P, 600 ml). The fraction eluted with a methanol solution containing 40% water gave the crude compound (IX) 8.87 g. Purification with a silica gel column chromatography (mixed solution of chloroform-methanol) and freeze-drying gave compound (IX) 5.37 g (35.7%).

Mp:192–194° C.

$[\alpha]_D$=-1.9° (c=1.005, $H_2O$, 25° C.)

IR(KBr)$cm^{-1}$: 1755, 1675, 1625, 1541, 1516, 1448, 1232, 1097.

NMR($CD_3OD$):8.97(1H, t, J=2.1 Hz), 7.34(1H, t, J=2.1 Hz), 5.19 and 5.04(total 1H, each t, J=7.5 Hz), 4.92(1H, dq, J=6.6 and 8.7 Hz), 4.36 and 4.35(1H, d, J=8.7 Hz), 4.07 and 3.92(total 1H, each m), 3.78(1H, m), 3.42(1H, m), 3.22(2H, m), 1.5–2.0(4H, m), 1.28 and 1.22(total 3H, each d, J=6.6 Hz), 1.21 and 1.02(total 3H, each d, J=6.6 Hz).

Elemental analysis ($C_{16}H_{22}N_4O_4S \cdot H_2O$)

Calcd.: C,49.99;H,6.29;N,14.57;S,8.34.

Found: C,49.99;H,6.29;N,14.79;S,8.36.

Test Example

Test Example 1

The enhancing effects of compound (IX) on the spontaneous locomotor activity were examined in normal mice.

Methods:

Compound (IX) was orally administrated to C57BL/6 mice (male) and the spontaneous locomotor activity was measured with a locomotor activity measuring apparatus (SCANET, TOYO sangyo). Mice were familiarized to the cage of the apparatus for at least 60 min. Compound (IX) (1,3,10 mg/kg) or vehicle (vehicle, distilled water Otsuka) was administrated orally. The spontaneous locomotor activity was measured for 5 hours after the mice were returned to the cage. The results were shown in Table 1 and FIG. 1.

Figure 1:
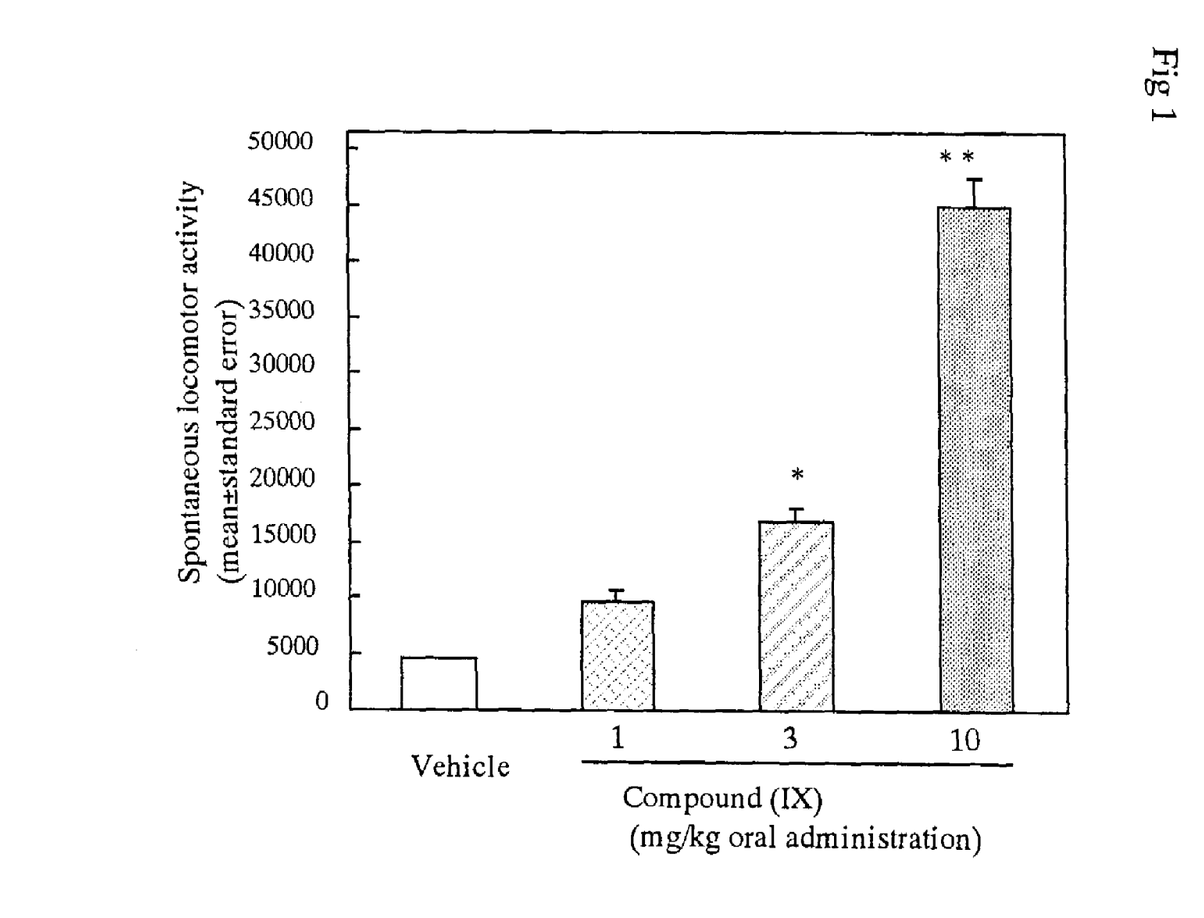
FIG. 1 shows an enhancing effect on the spontaneous locomotor activity in oral administration of the compound (IX) to normal mice.

As shown in Table 1 and FIG. 1, compound (IX) increased the spontaneous locomotor activity at a dose of 3 mg/kg or above.

TABLE 1

| Time | Vehicle | 1 mg/kg | 3 mg/kg | 10 mg/kg |
|---|---|---|---|---|
| 60–30 | 1532 | 1016 | 2349 | 1700 |
| 30–0 | 1676 | 436 | 782 | 401 |
| 0–30 | 1980 | 3737 | 3755 | 5910 |
| 30–60 | 100 | 842 | 2626 | 5079 |
| 60–90 | 350 | 1178 | 2690 | 5485 |
| 90–120 | 162 | 1281 | 2632 | 6138 |
| 120–150 | 607 | 991 | 2230 | 5582 |
| 150–180 | 251 | 273 | 868 | 5390 |
| 180–210 | 150 | 411 | 377 | 4218 |
| 210–240 | 390 | 135 | 940 | 3297 |
| 240–270 | 247 | 463 | 266 | 2305 |
| 270–300 | 351 | 366 | 597 | 1457 |

TABLE 1-continued

| Time | Vehicle | 1 mg/kg | 3 mg/kg | 10 mg/kg |
|---|---|---|---|---|
| Total | 4586 | 9676 | 16941* | 44861** |
| SE | 824 | 1030 | 2630 | 5178 |

*$P < 0.05$, **$P < 0.01$ vs vehicle treatment (Tukey test).

Test Example 2

Mice injected intracerebroventricularly with a monoaminergic toxin, 6-OHDA were used as a model for Parkinson's disease. The effects of compound (IX) in single administration or in combination with L-DOPA were examined in 6-OHDA-treated mice, which exhibited significant reduction in spontaneous locomotor activity.

Methods:

To C57BL/6 mice (male) were administrated desipramine (desipramine (25 mg/kg, i.p., 0.5%), lactic acid) and 6-OHDA (40 μg/μl/mouse, 0.2% ascorbic acid) was injected in the cerebroventricule after 30 min. The mice were placed in the locomotor activity measuring apparatus after one day. Compound (IX) (0.3, 1 mg/kg), with or without L-DOPA (10 mg/kg, i.p., dissolved in 0.1N HCl and diluted with distilled water or injection, Otsuka Pharmaceutical), was administrated after 90 min, then the spontaneous locomotor activity was measured for 5 hours. When L-DOPA was administrated, mice were pre-treated with carbidopa (25 mg/kg, i.p., 0.5% lactic acid) before 30 min. The results were shown in Table 2 and FIG. 2.

Figure 2:
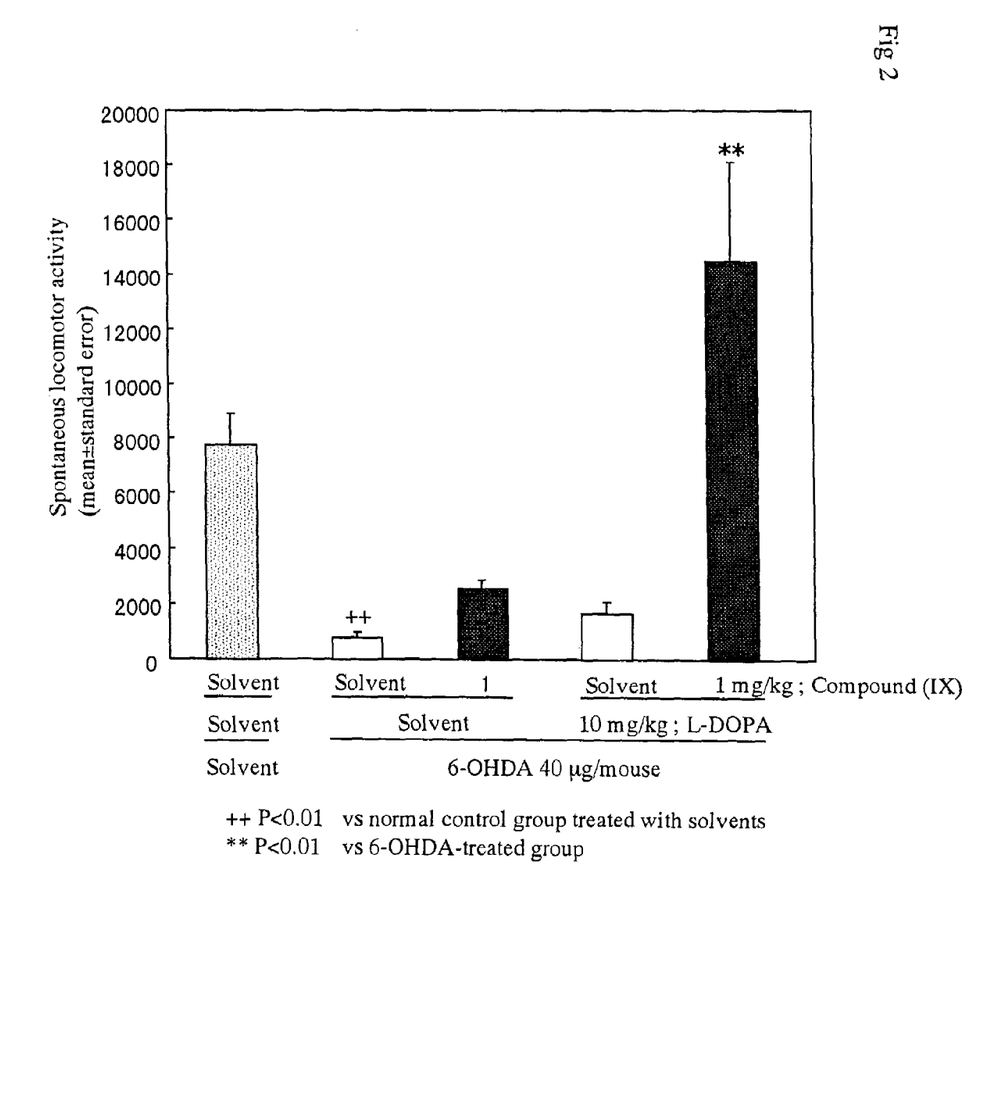
FIG. 2 shows an enhancing effect on the spontaneous locomotor activity of compound (IX) in combination with L-DOPA in mice injected intracerebroventricularly with 6-OHDA.

As shown in Table 2 and FIG. 2, the locomotor activity was reduced to 1/6 by the injection of 6-OHDA to the cerebroventricule in comparison with that of normal control. Although compound (IX) 1 mg/kg (p.o.) in single administration did not show significant increase in the spontaneous locomotor activity, combined administration with L-DOPA (10 mg/kg, i.p.), which did not have significant effects on the spontaneous locomotor activity, showed significant and remarkable increase in the spontaneous locomotor activity (synergistic effect).

TABLE 2

| Treatments | | No. of mice | Total |
|---|---|---|---|
| Solvent | Solvent | Solvent | 8 | 7750 ± 1164 |
| 6-OHDA | Solvent | Solvent | 8 | 788 ± 181++ |
| 6-OHDA | Compound (IX) | Solvent | 8 | 2512 ± 333 |
| 6-OHDA | Solvent | L-DOPA | 8 | 1655 ± 428 |
| 6-OHDA | Compound (IX) | L-DOPA | 8 | 14468 ± 3618** |

++$P < 0.01$ vs normal control group treated with solvents
**$P < 0.01$ vs 6-OHDA-treated group
(Dunnett test)

Test Example 3

The effects of compound (IX) in single administration and in combination with L-DOPA on cataleptic responses were examined in mice pre-treated with a monoamine-depleting drug, reserpine.

Methods:

Reserpine (5 mg/kg, i.p., Apoplon Inj, Daiichi Pharmaceutical) was administrated to ddy mice (male). On the next day, compound (IX) (0.3, 1, 3 mg/kg, p.o.) with or without L-DOPA (25, 100 mg/kg, i.p., dissolved in 0.1N HCl and diluted with distilled water for injection (Otsuka Pharmaceutical)) was administrated to the mice and catalepsy test was performed after 1 hour. When L-DOPA was administrated, mice were pre-treated with carbidopa (25 mg/kg, i.p., 0.5% lactic acid) before 30 min.

The forelimbs or hindlimbs of each mouse were placed on a 4.5 cm high horizontal bar and the time was measured (cut off time 30 sec) until both legs reach the floor. The cataleptic responses were scored as follows (less than 5 sec.: 0 point, 5 sec. to less than 10 sec.: 1 point, 10 sec to less than 15 sec.: 2 points, 15 sec. to than 20 sec.: 3 points, 20 sec. to less than 25 sec.: 4 points, 25 sec. to less than 30 sec.: 5 points, 30 sec. or more: 6 points).

For forelimbs, the scores for 3 repetitive tests were summated. For hindlimbs, the tests were performed 5 times and of which 3 scores were summated excluding the highest and lowest scores. The catalepsy scores were calculated as the total scores for forelimbs and hindlimbs. The results were shown in Table 3 and FIG. 3.

Figure 3:
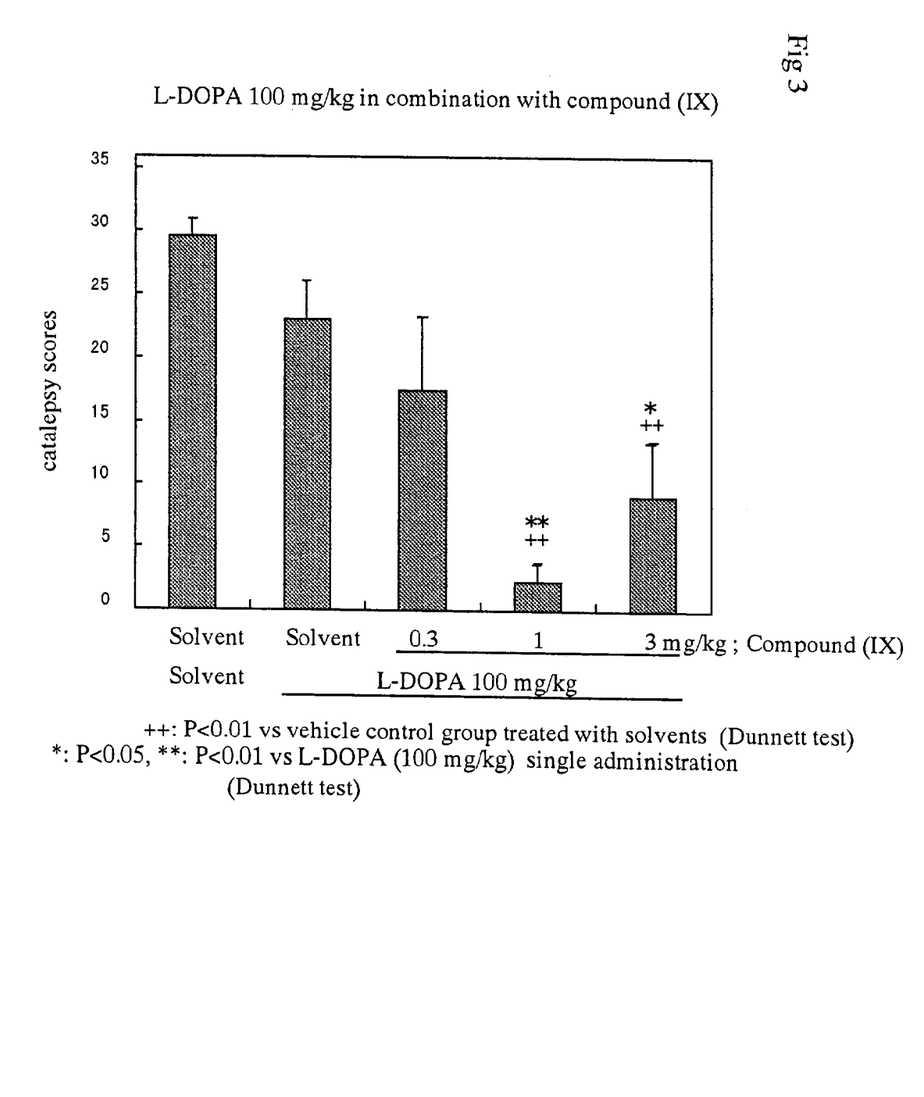
FIG. 3 shows a depression effect on reserpine-induced cataleptic posture of compound (IX) in combination with L-DOPA.

As shown in Table 3 and FIG. 3, compound (IX) (1,3 mg/kg, p.o.) in combination with L-DOPA (100 mg/kg, i.p.) exhibited significant depression effect on the reserpine-induced cataleptic posture.

TABLE 3

| i.p. | Solvent | L-DOPA 100 mg/kg Compound (IX) (mg/kg) | | |
|---|---|---|---|---|
| p.o. | Solvent | Solvent | 0.3 | 1 | 3 |
| mean | 29.6 | 23.0 | 17.4 | 2.3 | 9.2 |
| SD | 3.5 | 8.3 | 15.3 | 4.1 | 9.7 |
| No. of mice | 8 | 8 | 8 | 8 | 6 |

Test Example 4

Mice injected with a dopaminergic toxin, MPTP were used as a model for Parkinson's disease and the effects of single administration of compound (IX) on the reduction of the spontaneous locomotor activity caused by MPTP-treatment were examined.

Methods:

MPTP (40 mg/kg, i.p., saline) was injected twice at 24-hr intervals to C57BL/6 mice (male), and the day after the last administration, the mice were placed in locomotor activity measuring apparatus. After 30 min, compound (IX) alone (0.3, 1, 3 mg/kg, p.o.) was administered.

Figure 4:
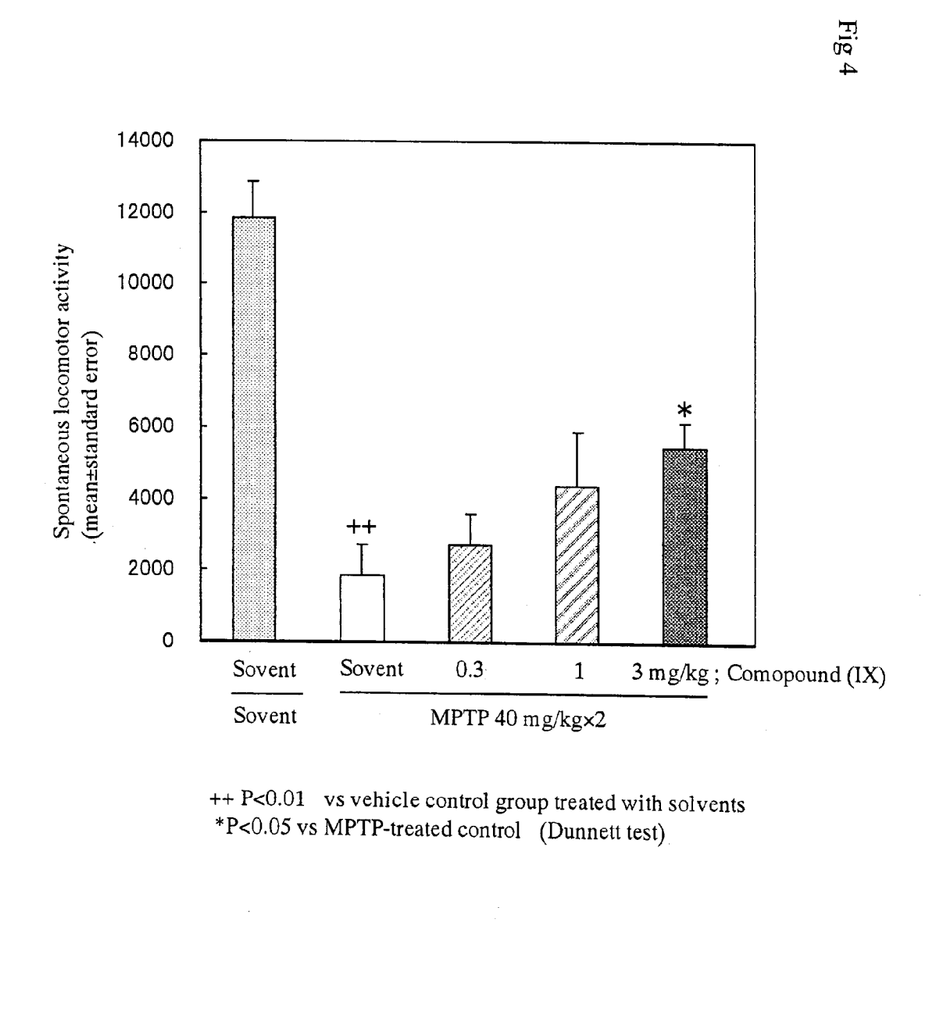
FIG. 4 shows an enhancing effect on the spontaneous locomotor activity in oral administration of the compound (IX) to MPTP-treated mice.

As shown in Table 4 and FIG. 4, compound (IX) (3 mg/kg, p.o.) alone significantly increased the spontaneous locomotor activity in mice with the reduced activity due to MPTP-treatment.

TABLE 4

| Treatments | | No. of mice | Total |
|---|---|---|---|
| Solvent | Solvent | 8 | 11844 ± 1030 |
| MPTP 40 mg/kg × 2 | Solvent | 8 | 1866 ± 841++ |
| MPTP 40 mg/kg × 2 | Compound (IX) 0.3 mg/kg | 8 | 2731 ± 875 |
| MPTP 40 mg/kg × 2 | Compound (IX) 1 mg/kg | 8 | 4370 ± 1507 |
| MPTP 40 mg/kg × 2 | Compound (IX) 3 mg/kg | 8 | 5463 ± 700* |

++$P < 0.01$ vs vehicle control group treated with solvents
*$P < 0.05$ vs MPTP-treated control group
(Dunnett test)

The above results revealed that orally administered compound (IX) alone or in combination with L-DOPA ameliorated the motor dysfunction, suggesting the usefulness for the treatment of Parkinson's disease.

Formulation Example

Formulation Example 1

Granules are prepared using the following ingredients.

| Ingredients | |
|---|---|
| The compound represented by the formula (I) | 10 mg |
| Lactose | 700 mg |
| Corn starch | 274 mg |
| HPC-L | 16 mg |
| | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | |
|---|---|
| The compound represented by the formula (I) | 10 mg |
| Lactose | 79 mg |
| Corn starch | 10 mg |
| Magnesium stearate | 1 mg |
| | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | |
|---|---|
| The compound represented by the formula (I) | 15 mg |
| Lactose | 90 mg |
| Corn starch | 42 mg |
| HPC-L | 3 mg |
| | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | |
|---|---|
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

Formulation Example 5

Sustained release tablets are prepared using the following ingredients.

| Ingredients | |
|---|---|
| The compound represented by the formula (I) | 15 mg |
| Lactose | 20 mg |
| Microcrystal cellulose | 100 mg |
| Magnesium stearate | 5 mg |
| Lovely wax-120 H | 110 mg |
| | 250 mg |

The compound represented by the formula (I), lactose, and microcrystal cellulose are made pass through a 60 mesh sieve and are mixed. Mixpowders are heated and solubilized with lovely wax-120 H (Froint Inds.) and then granulated. Magnesium stearate previously made pass through a 60 mesh sieve is added to the obtained granules and the resulting granules are compressed to yield sustained-release tablets.

Formulation Example 6

Sustained release double layered tablet are prepared using the following ingredients.

| Ingredients | |
|---|---|
| Immediately release layer | |
| The compound represented by the formula (I) | 15 mg |

-continued

| Ingredients | |
|---|---|
| Lactose | 25 mg |
| Microcrystal cellulose | 100 mg |
| Methylcellulose | 5 mg |
| Magnesium stearate | 5 mg |
| | 150 mg |
| Sustained release layer | |
| The compound represented by the formula (I) | 15 mg |
| Lactose | 25 mg |
| Microcrystal cellulose | 90 mg |
| Stearic acid | 10 mg |
| Methylcellulose | 5 mg |
| Magnesium stearate | 5 mg |
| | 150 mg |

Immediately release layer: The compound represented by the formula (I), lactose, and microcrystal cellulose are made pass through a 60 mesh sieve and are mixed. A solution of methylcellulose is added to the mixture and the resulting mixture is kneaded, granulated, and dried to yield the granules.

Sustained release layer: The compound represented by the formula (I), lactose, and microcrystal cellulose are made pass through a 60 mesh sieve and are mixed. Stearic acid is added to the mixture and the resulting mixture is heated and dissolved. They are kneaded, are granulated, and are dried to yield the granules.

Double layered tablet formation: Magnesium stearate is added to the granules of immediately release layer and the resulting mixture is compressed. Subsequently, magnesium stearate is added to the granules of sustained release layer and the resulting mixture is compressed on to yield sustained release double layered tablets.

Formulation Example 7

Enteric coated granules are prepared using the following ingredients.

| Ingredients | |
|---|---|
| The compound represented by the formula (I) | 30 mg |
| Microcrystal cellulose | 125 mg |
| Corn starch | 50 mg |
| CMC-Na | 25 mg |
| HPC or MC | 10 mg |
| | 240 mg |
| (Coating solution) | |
| HP-55 | 10.5 mg |
| Fatty acid ester of glycerin | 2.0 mg |
| Ethanol | 41.0 mg |
| Dichloromethane | 46.5 mg |
| Talc | 4 mg |

The active ingredient, microcrystal cellulose, corn starch, and CMC-Na are made pass through a 20 mesh sieve and mixed thoroughly. A solution of HPC (hydroxypropyhlcellulose) or MC (methylcellulose) is added to the mixture and the kneading is made pass through a 16 mesh sieve. The obtained granules are dried at 50 to 60° C. The dried granules are spray-coated with a solution of HP-55 (hydroxypropylmethylcellulose phthalate, Shinetsu Kagaku inc.) in fatty acid ester of glycerin, ethanol, dichloromethane, and talc to yield the enteric coated granules.

Formulation 8

Enteric coated granules are prepared using the following ingredients.

| Ingredients | |
|---|---|
| The compound represented by the formula (I) | 30 mg |
| Microcrystal cellulose | 155 mg |
| Corn starch | 60 mg |
| CMC-Na | 25 mg |
| HPC or MC | 5 mg |
| | 275 mg |
| (Coating solution) | |
| Eudragit L30D-55 | 46.8 mg |
| Polysolvate 80 | 0.7 mg |
| PEG 6000 | 1.4 mg |
| Talc | 4.2 mg |
| Purified water | 46.8 mg |

The granules which are prepared in a manner similar to that described in the method of Formulation example 7 is coated with the coating solution comprising the solution of Eudragit L30D-55 (Röhm Pharma) in polysolvate 80 (polyoxyethylenesorbitan monooleate, Kao inc.), PEG 6000 (polyethylene glycol, macrogoal 6000, Macrogol 6000, Lion Corporation), talc, and purified water. After the obtained granules are dried, the resulting granules are made pass through a 16 mesh sieve to yield the enteric coated granules.

Formulation Example 9

Sublingual tablets are prepared using the following ingredients.

| Ingredients | |
|---|---|
| The compound represented by the formula (I) | 10 mg |
| Lactose | 70 mg |
| Corn starch | 12 mg |
| Methylcellulose | 5 mg |
| Talc | 2 mg |
| Magnesium stearate | 1 mg |
| | 100 mg |

The compound represented by the formula (I), lactose, and corn starch are made pass through a 80 mesh sieve and mixed. Mixpowder is kneaded with methylcellulose solution and granulated, dried, then the granules are lubricated. The mixture of the resulting granules with talc and magnesium stearate which are made pass through a 60 mesh sieve is tableted to obtain sublingual tablets.

Formulation Example 10

Injections are prepared using the following ingredients.

| Ingredients | |
|---|---|
| The compound represented by the formula (I) | 1 mg |
| Glucose | 2 mg |
| Water for injection | 997 mg |
| | 1000 mg |

The above ingredients are filled into ampoules.

Formulation 11

Freeze-dried injections are prepared using the following ingredients.

| Ingredients | |
|---|---|
| The compound represented by the formula (I) | 1 mg |
| D-mannitol | 200 mg |
| Water for injection | 779 mg |
| | 1000 mg |

The above ingredients are filled into ampoules for freeze-drying and the ampoules are freeze-dried to yield the freeze-dried injections.

Formulation 12

Suppositories are prepared using the following ingredients.

| Ingredients | |
|---|---|
| The compound represented by the formula (I) | 30 mg |
| Witepsol | 1470 mg |
| | 1500 mg |

The compound represented by the formula (I) is made pass through a 60 mesh sieve. The compound is dispersed in the solution of the melted witepsol (higher fatty acid triglyceride, Mitsuba Boueki) at 50 to 60° C. The solution is cooled to 38 to 40° C. with stirring to yield the medical fluid. The medical fluid is filled into a container of aluminum foil, sealed, and then cooled to yield the suppositories.

Formulation Example 13

Nasals are prepared using the following ingredients.

| Ingredients | |
|---|---|
| The compound represented by the formula (I) | 2 mg |
| Carboxyvinylpolymer | 5 mg |
| L-Arginine | 10 mg |
| Sodium chloride | 0.6 mg |
| Purified water | 84.2 mg |
| | 100 mg |

After the compound represented by the formula (I) is dissolved in carboxyvinylpolymer, L-arginine and sodium chloride is added to the solution. The solution's pH is adjusted and the mucosity is adjusted by adding purified water to yield the objective medical fluid.

Formation Example 14

Endermatic formulation is prepared using the following ingredients.

| Ingredients | |
|---|---|
| The compound represented by the formula (I) | 10 mg |
| Isopropyl myristate | 990 mg |
| | 1000 mg |

After the compound represented by the formula (I) is dispersed in isopropyl myristate, the mixture is mixed with acrylic adhesive formulation (e.g. nikazole) and is attached plastered to a support to yield endermatic formulation.

Formulation Example 15

Ointment was prepared using the following ingredients.

| Ingredients | |
|---|---|
| The compound represented by the formula (I) | 10 mg |
| Liquid paraffin | 7.5 mg |
| Glycerol | 82.5 mg |
| | 100 mg |

The compound represented by the formula (I) is dispersed in liquid paraffin and kneaded with white petrolatum to yield the ointment.

INDUSTRIAL APPLICABILITY

A TRH derivative is useful as a pharmaceutical composition orally administrated for treating or preventing Parkinson's disease, especially for exhibiting a synergic effect in combination with L-DOPA.

The invention claimed is:

1. A method of treating a mammal, including a human, to alleviate the pathological effects of Parkinson's disease, which comprises administering to said mammal in a pharmaceutically effective amount to alleviate said effects, a compound of formula (IX):

(IX)

or a pharmaceutically acceptable salt or solvate thereof.

2. A method for enhancing an activity of L-DOPA administered to a mammal, including a human, which comprises administering to said mammal in a pharmaceutically effective amount to enhance the activity of L-DOPA (a) L-DOPA and (b) a compound of the formula (IX):

(IX)

or a pharmaceutically acceptable salt or solvate thereof.

3. The method as claimed in claim 2 wherein the combination of (a) L-DOPA and (b) a compound of formula (IX) has a synergistic effect.

* * * * *